United States Patent
Heymann et al.

(10) Patent No.: US 8,710,407 B2
(45) Date of Patent: Apr. 29, 2014

(54) SELECTIVE THERMAL TREATMENT OF MEDICAL INSTRUMENT PORTIONS WITH THERMAL TREATMENT SYSTEM INSTRUMENT HOLDER

(75) Inventors: Bruce Heymann, Vienna, VA (US); Ray Tsang, Herndon, VA (US); Durward I. Faries, Jr., McLean, VA (US); Tracy Augustine, legal representative, McLean, VA (US)

(73) Assignee: Ecolab USA Inc., St Paul, MN (US)

( * ) Notice: Subject to any disclaimer, the term of this patent is extended or adjusted under 35 U.S.C. 154(b) by 290 days.

(21) Appl. No.: 13/223,378

(22) Filed: Sep. 1, 2011

(65) Prior Publication Data

US 2012/0187104 A1    Jul. 26, 2012

Related U.S. Application Data

(60) Provisional application No. 61/379,547, filed on Sep. 2, 2010.

(51) Int. Cl.
*A61B 19/10* (2006.01)
*A61F 7/00* (2006.01)
*F27D 11/00* (2006.01)

(52) U.S. Cl.
USPC ........... 219/385; 219/430; 219/433; 219/439; 604/114

(58) Field of Classification Search
None
See application file for complete search history.

(56) References Cited

U.S. PATENT DOCUMENTS

| | | | |
|---|---|---|---|
| 2,174,425 | A | 9/1939 | Schlumbohm |
| 2,323,356 | A | 7/1943 | Rosay |
| 2,599,192 | A | 6/1952 | Miller |
| 2,613,511 | A | 10/1952 | Walsh |
| 2,807,701 | A | 9/1957 | Conlin et al. |
| 3,249,070 | A | 5/1966 | Day et al. |
| 3,685,507 | A | 8/1972 | Donnelly |
| 3,807,954 | A | 4/1974 | McDonald |
| 3,869,596 | A | 3/1975 | Howie |
| 3,902,484 | A | 9/1975 | Winters |
| 3,942,510 | A | 3/1976 | Garrett |
| 4,053,954 | A | 10/1977 | Chapman |
| 4,270,067 | A | 5/1981 | Thomas et al. |
| 4,284,880 | A | 8/1981 | Keiser |
| 4,393,659 | A | 7/1983 | Keyes et al. |

(Continued)

FOREIGN PATENT DOCUMENTS

| | | |
|---|---|---|
| JP | 61185967 | 11/1986 |
| JP | 61123532 | 5/1994 |

OTHER PUBLICATIONS

PCT International Search Report and the Written Opinion, PCT/IB2011/053839, Apr. 4, 2012, 10 pages.

*Primary Examiner* — Joseph M Pelham
(74) *Attorney, Agent, or Firm* — Edell, Shapiro & Finnan, LLC

(57) ABSTRACT

A thermal treatment system for thermally treating objects includes a housing including a top surface, a basin recessed into the top surface and configured to contain a liquid medium, where the liquid medium thermally treats objects placed within the liquid medium, and a ramp structure disposed on the top surface of the housing. The ramp structure is configured to support at least one object such that a first end portion of the object is disposed within the liquid medium while a second end portion of the object is supported by the ramp structure outside of the liquid medium.

31 Claims, 11 Drawing Sheets

(56) References Cited

U.S. PATENT DOCUMENTS

| | | |
|---|---|---|
| 4,458,139 A | 7/1984 | McClean |
| 4,474,016 A | 10/1984 | Winchell |
| 4,516,564 A | 5/1985 | Koiso et al. |
| 4,522,041 A | 6/1985 | Menzel |
| 4,625,098 A | 11/1986 | Joe |
| 4,782,835 A | 11/1988 | Bernardini |
| 4,828,876 A | 5/1989 | Ohhara et al. |
| 4,869,271 A | 9/1989 | Idris |
| 4,903,710 A | 2/1990 | Jessamine et al. |
| 4,934,152 A | 6/1990 | Templeton |
| 4,967,061 A | 10/1990 | Weber, Jr. et al. |
| 5,040,699 A | 8/1991 | Gangemi |
| 5,042,455 A | 8/1991 | Yue et al. |
| 5,042,981 A | 8/1991 | Gross |
| RE33,854 E | 3/1992 | Adair |
| 5,129,033 A | 7/1992 | Ferrara et al. |
| 5,163,299 A | 11/1992 | Faries, Jr. et al. |
| 5,174,306 A | 12/1992 | Marshall |
| 5,310,524 A | 5/1994 | Campbell et al. |
| 5,331,820 A | 7/1994 | Faries, Jr. et al. |
| 5,333,326 A | 8/1994 | Faries, Jr. et al. |
| 5,345,063 A | 9/1994 | Reusche et al. |
| 5,351,675 A | 10/1994 | Brodsky |
| 5,363,746 A | 11/1994 | Gordon |
| 5,374,278 A | 12/1994 | Chesterfield et al. |
| 5,374,813 A | 12/1994 | Shipp |
| 5,383,476 A | 1/1995 | Peimer et al. |
| 5,386,835 A | 2/1995 | Elphick et al. |
| 5,396,905 A | 3/1995 | Newman |
| 5,400,267 A | 3/1995 | Denen et al. |
| 5,400,616 A | 3/1995 | Faries, Jr. et al. |
| 5,402,644 A | 4/1995 | Faries, Jr. et al. |
| 5,429,801 A | 7/1995 | Faries, Jr. et al. |
| 5,435,322 A | 7/1995 | Marshall |
| 5,443,082 A | 8/1995 | Mewburn |
| 5,449,892 A | 9/1995 | Yamada |
| 5,457,962 A | 10/1995 | Faries, Jr. et al. |
| 5,463,213 A | 10/1995 | Honda |
| 5,480,302 A | 1/1996 | Fife |
| 5,502,980 A | 4/1996 | Faries, Jr. et al. |
| 5,517,170 A | 5/1996 | Peters et al. |
| 5,518,502 A | 5/1996 | Kaplan et al. |
| 5,522,095 A | 6/1996 | Faries, Jr. et al. |
| 5,522,805 A | 6/1996 | Vancaillie et al. |
| 5,524,478 A | 6/1996 | Joy et al. |
| 5,524,643 A | 6/1996 | Faries, Jr. et al. |
| 5,531,697 A | 7/1996 | Olsen |
| 5,539,185 A | 7/1996 | Polster |
| 5,549,543 A | 8/1996 | Kim |
| 5,551,240 A | 9/1996 | Faries, Jr. et al. |
| 5,615,423 A | 4/1997 | Faries, Jr. et al. |
| 5,647,840 A | 7/1997 | D'Amelio et al. |
| 5,651,757 A | 7/1997 | Meckstroth |
| 5,653,938 A | 8/1997 | Faries, Jr. et al. |
| 5,658,478 A | 8/1997 | Roeschel et al. |
| 5,664,582 A | 9/1997 | Szymaitiz |
| 5,715,547 A | 2/1998 | Becker et al. |
| 5,717,188 A | 2/1998 | Vaillancourt |
| 5,800,352 A | 9/1998 | Ferre et al. |
| 5,809,788 A | 9/1998 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 5,910,106 A | 6/1999 | Morgan et al. |
| 5,950,438 A | 9/1999 | Faries, Jr. et al. |
| D417,809 S | 12/1999 | Hofman |
| 6,003,328 A | 12/1999 | Faries, Jr. et al. |
| 6,035,855 A | 3/2000 | Faries, Jr. et al. |
| 6,087,636 A | 7/2000 | Faries, Jr. et al. |
| 6,091,058 A | 7/2000 | Faries, Jr. et al. |
| 6,102,044 A | 8/2000 | Naidyhorski |
| D441,996 S | 5/2001 | Wright |
| 6,231,596 B1 | 5/2001 | Collins |
| 6,234,635 B1 | 5/2001 | Seitzinger et al. |
| 6,255,627 B1 | 7/2001 | Faries, Jr. et al. |
| 6,259,067 B1 | 7/2001 | Faries et al. |
| D447,900 S | 9/2001 | Wright |
| 6,341,704 B1 | 1/2002 | Michel, Jr. |
| 6,371,121 B1 | 4/2002 | Faries, Jr. et al. |
| 6,448,571 B1 | 9/2002 | Goldstein |
| 6,586,950 B1 | 7/2003 | Sargent et al. |
| 6,593,552 B1 | 7/2003 | Li |
| 6,644,383 B2 | 11/2003 | Joseph et al. |
| 6,701,174 B1 | 3/2004 | Krause et al. |
| 6,810,881 B2 | 11/2004 | Faries, Jr. et al. |
| 6,860,271 B2 | 3/2005 | Faries, Jr. et al. |
| 6,884,970 B2 | 4/2005 | Lehman |
| 6,910,485 B2 | 6/2005 | Faries, Jr. et al. |
| 6,918,395 B2 | 7/2005 | Faries, Jr. et al. |
| 6,927,365 B2 | 8/2005 | Li |
| 7,041,941 B2 | 5/2006 | Faries, Jr. et al. |
| 7,128,275 B2 | 10/2006 | Kammer et al. |
| 7,176,030 B2 | 2/2007 | Faries, Jr. et al. |
| 7,276,675 B2 | 10/2007 | Faries, Jr. et al. |
| 7,307,245 B2 | 12/2007 | Faries, Jr. et al. |
| 7,309,472 B2 | 12/2007 | Michaelson et al. |
| 7,311,660 B2 | 12/2007 | Gomez |
| 7,347,210 B2 | 3/2008 | Faries, Jr. et al. |
| 7,350,373 B1 | 4/2008 | Faries, Jr. et al. |
| 7,417,205 B2 | 8/2008 | Faries, Jr. et al. |
| 7,418,966 B2 | 9/2008 | Faries, Jr. et al. |
| 7,560,667 B2 | 7/2009 | Kammer |
| 7,671,302 B1 | 3/2010 | Faries, Jr. et al. |
| 7,728,262 B1 | 6/2010 | Faries, Jr. et al. |
| 7,811,522 B2 * | 10/2010 | Mathus et al. ............. 422/400 |
| 7,854,230 B2 | 12/2010 | Faries, Jr. et al. |
| 7,959,860 B2 | 6/2011 | Faries, Jr. et al. |
| 8,148,666 B2 | 4/2012 | Faries, Jr. et al. |
| 8,148,667 B2 * | 4/2012 | Faries et al. ............. 219/429 |
| 8,153,937 B2 * | 4/2012 | Faries et al. ............. 219/429 |
| 2003/0132216 A1 | 7/2003 | Li |
| 2003/0231990 A1 | 12/2003 | Faries, Jr. et al. |
| 2004/0200480 A1 | 10/2004 | Faries, Jr. et al. |
| 2004/0200483 A1 | 10/2004 | Faries, Jr. et al. |
| 2004/0208780 A1 | 10/2004 | Faries, Jr. et al. |
| 2004/0225265 A1 * | 11/2004 | Tapadiya ............. 604/317 |
| 2005/0247169 A1 | 11/2005 | Faries, Jr. et al. |
| 2006/0065276 A1 | 3/2006 | Kammer et al. |
| 2006/0086361 A1 | 4/2006 | Kammer et al. |
| 2006/0091128 A1 | 5/2006 | Kammer et al. |
| 2006/0091129 A1 | 5/2006 | Colonna |
| 2006/0194324 A1 | 8/2006 | Faries, Jr. et al. |
| 2006/0260443 A1 | 11/2006 | Faries, Jr. et al. |
| 2006/0271017 A1 * | 11/2006 | Booth et al. ............. 604/540 |
| 2006/0289445 A1 | 12/2006 | Colonna |
| 2007/0089753 A1 | 4/2007 | Faries, Jr. et al. |
| 2008/0152937 A1 * | 6/2008 | Kammer et al. ............. 428/543 |
| 2009/0061053 A1 * | 3/2009 | Gaylor et al. ............. 426/107 |
| 2009/0255540 A1 | 10/2009 | Faries, Jr. et al. |
| 2010/0116810 A1 | 5/2010 | Faries, Jr. et al. |
| 2010/0200561 A1 | 8/2010 | Faries, Jr. et al. |
| 2011/0270367 A1 | 11/2011 | Faries, Jr. et al. |

* cited by examiner

SELECTIVE THERMAL TREATMENT OF MEDICAL INSTRUMENT PORTIONS WITH THERMAL TREATMENT SYSTEM INSTRUMENT HOLDER

CROSS REFERENCE TO RELATED APPLICATION

The present application claims priority from U.S. Provisional Patent Application Ser. No. 61/379,547, entitled "Thermal Treatment System Instrument Holder and Method of Selectively Thermally Treating Medical Instrument Portions" and filed Sep. 2, 2010, the disclosure of which is incorporated herein by reference in its entirety.

BACKGROUND

1. Field of the Invention

The present invention pertains to thermally treating objects, such as surgical instruments.

2. Discussion of the Related Art

Surgical scopes (e.g., laparoscopes, endoscopes, arthroscopes, etc.) are used in corrective medical procedures, as well as in medical procedures that image interior viscera such as surfaces of the stomach, small intestines, and colon. The use of surgical scopes permits a surgeon to view a patient body interior with a minimal amount of cutting of patient tissue. The surgical scopes may be warmed prior to use, where scope optics must remain dry to protect those optics and prevent distortion of the image. The scopes are warmed for several reasons, including enhancing image results, preventing infections, and maintaining normothermia. For example, a scope that is unwarmed prior to being inserted into a patient body may fog due to differences between the body temperature and scope temperature, thereby impeding or distorting the resulting image. Further, scopes may be warmed to minimize trauma caused to tissue in response to insertion of the scope into the patient body. The trauma basically results from the temperature difference between the scope and the tissue. Inserting a hot or cold scope may damage tissue, thereby leading to infections. Inserting a cold scope may also lower core body temperature, thereby leading to hypothermia and compromising patient safety.

Scopes can be warmed in an insulated container (e.g., THERMOS) filled with warm liquid. However, since the container generally does not provide temperature control for the liquid and/or scopes, the temperature of the scope is not precisely known by medical personnel. Accordingly, medical personnel may utilize scopes at inadequate temperatures relative to a patient body, thereby potentially causing tissue trauma, fogging of the scope as described above, and/or hypothermia. A chemical wipe or spray may be used to reduce fogging instead of warming the scopes; however, the chemical may be inadvertently introduced into the patient, thereby causing complications. In addition, when an insulated container is used, the scope may be damaged when it, by necessity, comes in contact with the sides and/or bottom of the container.

SUMMARY

In accordance with an example embodiment of the present invention, a thermal treatment system for thermally treating objects comprises a housing including a top surface, a basin recessed into the top surface and configured to contain a liquid medium, where the liquid medium thermally treats objects placed within the liquid medium, and a ramp structure disposed on the top surface of the housing. The ramp structure is configured to support at least one object such that a first end portion of the object is disposed within the liquid medium while a second end portion of the object is supported by the ramp structure outside of the liquid medium. The object can comprise a scope including a camera disposed at the second end portion of the scope, where the camera is supported by the ramp structure and maintained in a dry state during thermal treatment of at least the first end portion of the scope that is submerged within the liquid medium.

In accordance with another example embodiment of the present invention, a surgical drape kit for use in a thermal treatment system including a housing with a top surface and a basin recessed within the housing top surface to contain and thermally treat a liquid medium, the drape kit comprising a drape suitably dimensioned to cover and hang down from the top surface of the housing, the drape being disposed within and conforming to the basin to form a drape receptacle, and a ramp structure configured to be secured on the top surface of the housing. The ramp structure is configured to support at least one object such that a first end portion of the object is disposed within the liquid medium while a second end portion of the object is supported by the ramp structure outside of the liquid medium.

In accordance with a further example embodiment of the present invention, in a thermal treatment system including a housing with a top surface, a basin recessed into the top surface and configured to contain a liquid medium, and a ramp structure disposed on the top surface of the housing, a method of selectively thermally treating objects comprises receiving an object within the basin such that a first end portion of the object is disposed within the liquid medium while a second end portion of the object is supported by the ramp structure outside of the liquid medium, and thermally treating at least the first end portion of the object submerged within the liquid medium.

The above and still further features and advantages of the present invention will become apparent upon consideration of the following detailed description of example embodiments thereof, particularly when taken in conjunction with the accompanying drawings wherein like reference numerals in the various figures are utilized to designate like components.

DETAILED DESCRIPTION

In accordance with example embodiments of the present invention, systems and corresponding methods are described herein for thermally treating objects, such as warming of surgical scopes, in a temperature controlled liquid medium or bath while maintaining portions of the objects, such as the optics of a scope, in a dry state. In an example embodiment, a system includes a cabinet including a shelf or ledge to support components of the scope, a basin positioned within the cabinet to contain and thermally treat a liquid bath, and a ramp structure disposed on the shelf of the cabinet that supports exposed scope optics above the liquid bath within the basin. The scope optics reside outside of the bath in a dry state, thereby permitting the remaining scope portions within the bath to be thermally treated. This enables retrieval of enhanced images by the scope during a medical procedure. The system can further include a tray configured for insertion within the basin to protect a surgical drape used in combination with the system from being punctured by surgical instruments placed within the liquid bath. The tray can also include additional features such as apertures or holes provided within the tray to facilitate circulation of fluid within the basin during system operation.

Figure 1:
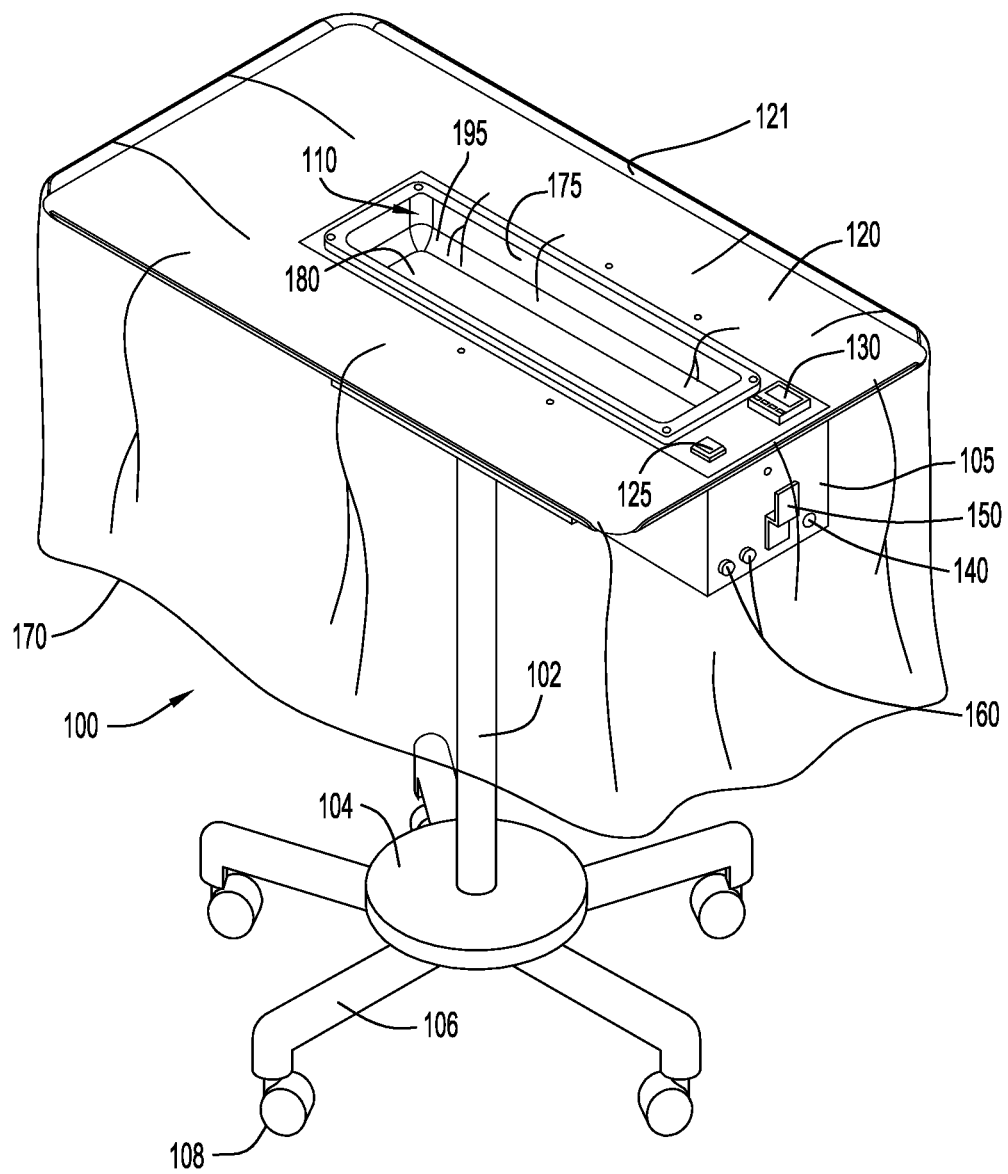
FIG. 1 illustrates a perspective view of a thermal treatment system in accordance with an embodiment of the present invention.
Figure 10:
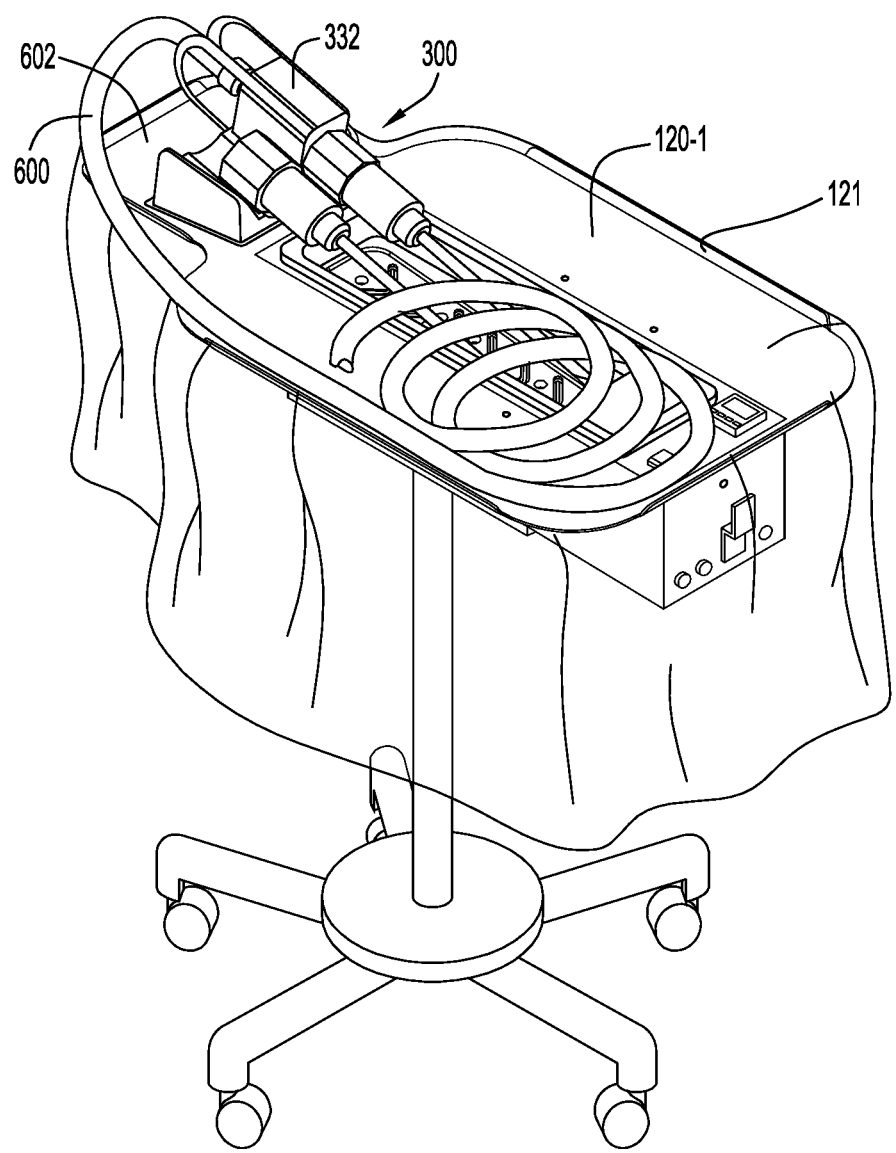
FIGS. 10-12 illustrate perspective views of a support assembly for a surgical instrument and tray coupled with a thermal treatment system according to additional embodiments of the invention.
Figure 11:
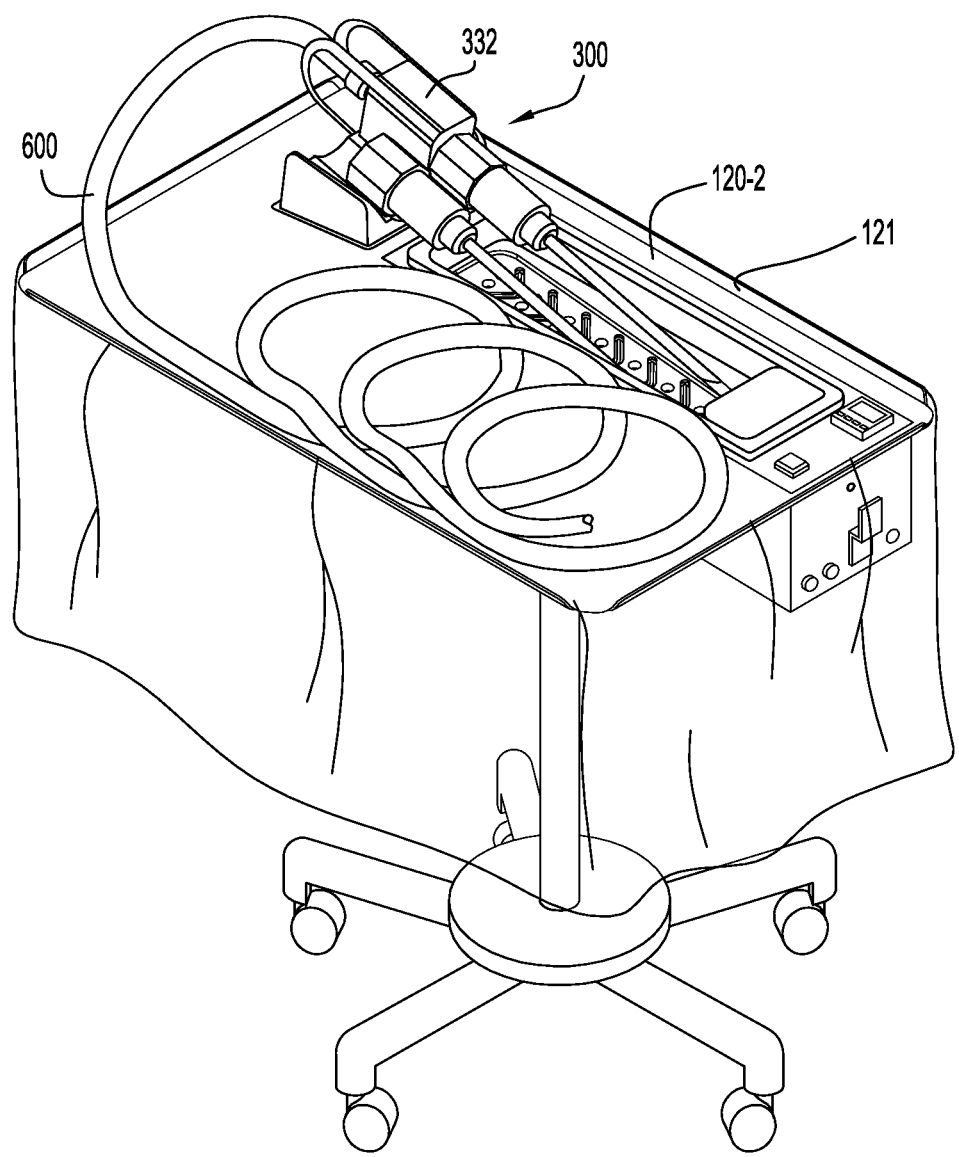
Figure 12:
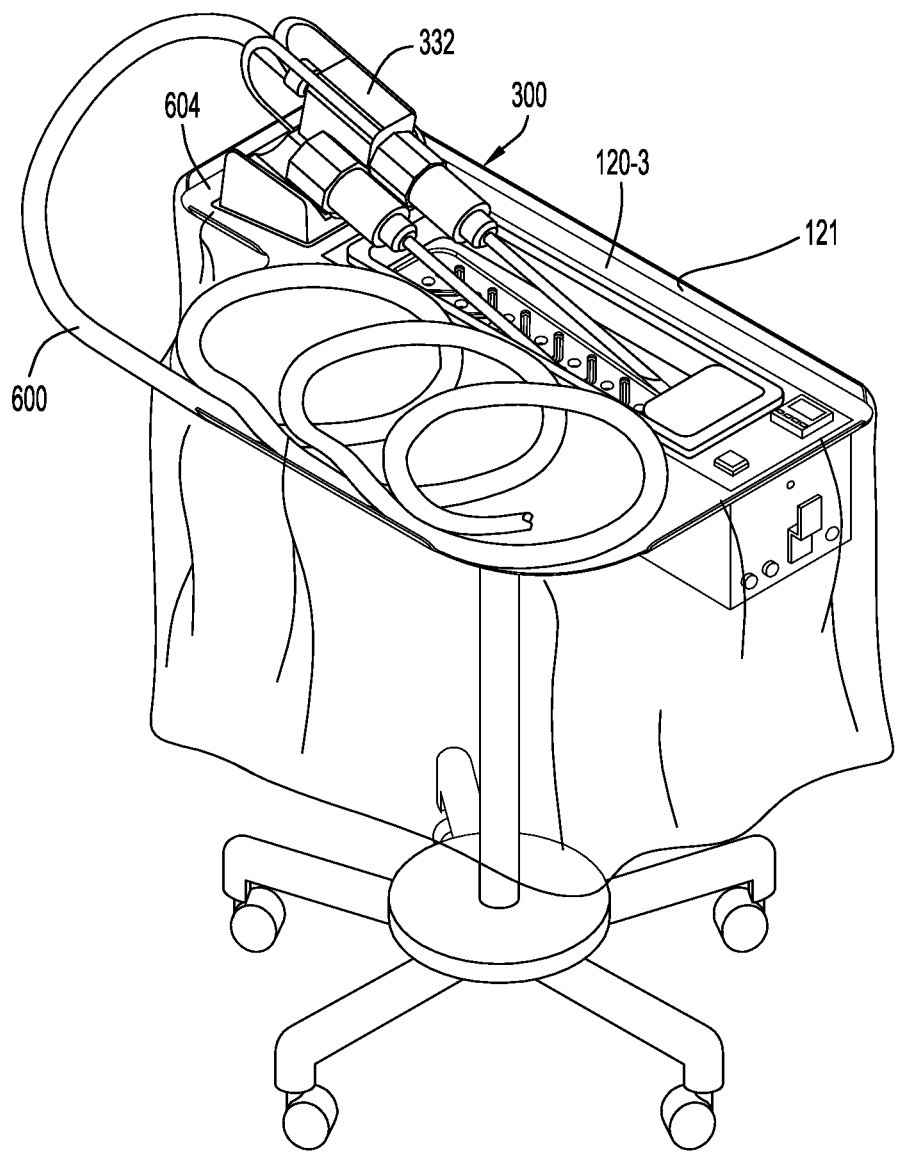

An example embodiment of a system for thermally treating a sterile medium (e.g., solution or liquid) is illustrated in FIG. 1. As shown, the thermal treatment system 100 includes a cabinet formed by a housing 105 which is in the form of a generally rectangular block defined by a lower wall and side walls of the housing. A top surface or shelf 120 of the cabinet overlays the rectangular housing 105 and has length and width dimensions that extend beyond at least one side wall of the housing 105 so as to provide suitable surface areas for placement of items associated with surgical instruments that are treated by the system. As shown in the embodiment of FIG. 1, the shelf 120 is generally rectangular and is situated over housing 105 such that a central lengthwise axis of the shelf 120 corresponds with a central lengthwise axis of the housing 105, thus forming ledge sections of the shelf 120 that extend beyond both longitudinal side walls of the housing 105. However, the shelf can be designed with any other suitable geometric configurations and/or spatial arrangements with respect to the cabinet housing, and some additional non-limiting examples are depicted in FIGS. 10-12 and described in further detail below. The shelf 120 can also include a raised edge 121 disposed along one or more sides of the shelf, where the one or more raised edges 121 help to stabilize the support of items placed on the shelf during system operation.

The cabinet housing 105 attaches, via the lower housing wall, to one end of a support post 102. The support post 102 attaches at its other end to a generally circular base 104, and the base 104 includes a plurality of legs 106 (e.g., five legs 106 as shown in FIG. 1) that extend transversely from and at circumferentially spaced locations along the base 104. Each leg 106 includes a caster wheel 108 disposed at its free end to facilitate movement of the system 100 in a variety of different directions, thus enabling easy mobility of the system. However, it is noted that the system can include any other suitable support structure that supports the system at a suitable elevation and optionally facilitates movement of the system to different locations.

A warming basin 110 is provided in a recess that is defined through an opening in the shelf 120 and extending within the housing 105 of the cabinet. The basin 110 may be of any suitable size and/or shape; however, by way of example only, the basin is illustrated having a substantially rectangular shape including an open top structure with generally vertical side walls 175 extending up from a generally horizontal floor 180.

A heater power switch 125 and a temperature controller/indicator 130 are provided on the top surface 120 of the cabinet housing 105, at a suitable location adjacent the warming basin 110. Optionally, a support hook 140 can be provided on a side wall of the cabinet housing 105 (e.g., a front wall of the housing 105 as viewed in FIG. 1) and may support a system power cord (not shown). Electrical connections may be made to the cabinet via a power port 150 disposed on the housing front wall adjacent the hook 140. In addition, fuse receptacles 160 may be disposed on the housing front wall proximate the hook 140 to receive fuses in order to prevent damage to circuitry (such as the circuitry similar to that illustrated in FIG. 2) contained within the cabinet housing 105.

A sterile drape 170, preferably transparent, may be disposed over the shelf 120 and sides of the housing 105. The power switch 125 and the controller 130, disposed on the shelf 120, are actuable manually through drape 170. The portion of the drape 170 disposed as a liner in the basin 110 serves as a sterile container or receptacle for a sterile medium 195 to be heated and placed therein. The sterile medium 195 treated by the thermal treatment system 100 may include, but is not limited to, sterile liquid comprising a 0.80% to 0.95% sodium chloride solution (i.e., saline). The drape 170 is preferably transparent and may be made from a material that is impervious to the sterile liquid and sufficiently soft and pliable to conform to the walls 175 and floor 180 of the basin 110. The thickness of the drape 170 is preferably minimized to render thermal transfer therethrough most efficient, yet the thickness is sufficient to resist tearing and puncturing during normal use. The drape 170 may be made of materials commonly used in hospitals for surgical drapes and has a thickness, by way of example only, of approximately 4.5 to 6.0 mils. The drape 170, however, may have any desired thickness. The drape 170 may also be made of polyurethane film as disclosed for the drape in U.S. Pat. No. 4,934,152 (Templeton), the disclosure of which is incorporated herein by reference in its entirety. In addition, the drape 170 may include sensors to detect the presence or absence of liquid within the basin and/or the presence of a drape leak. Examples of these types of drapes are disclosed in U.S. Pat. No. 6,810,881 (Faries, Jr. et al.) and U.S. Pat. No. 6,910,485 (Faries, Jr. et al.); as well as in U.S. Published Patent Application Nos. 2003/0231990 (Faries, Jr. et al.), 2004/0200483 (Faries, Jr. et al.), 2004/0200480 (Faries, Jr. et al.), and 2004/0208780 (Faries, Jr. et al.), the disclosures of which are incorporated herein by reference in their entireties.

The drape 170 may further include a preformed container portion or tray (described in further detail below) contoured to generally match the contour of the basin 110. The preformed container portion is typically thicker than the remaining portions of the drape described above in order to resist puncture and enable the container portion to maintain the shape of the basin 110. By way of example only, the container portion may be made of a heavy gauge polyethylene/ionomer resin blend having a thickness of approximately 10 to 16 mils. The percentage of ionomer resin in the blend is in the approximate range of forty to seventy percent. The drapes described above are designed to be disposable after a single use and are provided pre-sterilized and prepackaged in a manner to preserve its sterile state during storage. As further described below, the tray can be integral with the drape or, alternatively, separate from the drape. The tray can further be placed above or below the drape when placed within the housing basin during system operation.

The drape 170 is typically positioned over thermal treatment system 100 such that a portion of the drape is disposed in the basin 110 to form a drape receptacle. The drape 170 forms a sterile field above the basin to maintain sterility of a sterile liquid 195 placed in the drape receptacle. Generally, objects (e.g., medical instruments, containers, etc.) may be warmed in the basin by placing the objects in the heated liquid within the basin 110 (and contained by the drape receptacle).

Figure 2:
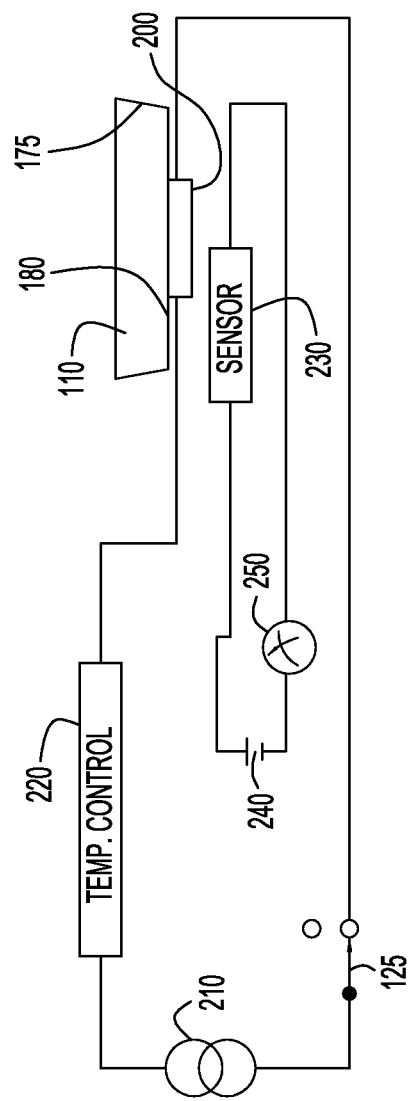
FIG. 2 illustrates an electrical schematic diagram of the heating unit employed by the thermal treatment system of FIG. 1.

The manner of heating sterile liquid in the warming basin 110 is illustrated schematically in FIG. 2. An electrical circuit includes a power source 210 connected in series with a temperature control unit 220, a heater element or pad 200, and the power control switch 125 (also illustrated in FIG. 1). The heater element 200 is typically a thin, wafer-like member disposed along the bottom surface of the warming basin 110, secured to the basin by a suitable pressure sensitive adhesive having efficient heat transfer characteristics. The heater element 200 has smaller dimensions than those of the basin floor 180 and is disposed at the approximate center of the basin bottom surface. Alternatively, the heater element 200 may be of any quantity (e.g., at least one), shape or size, and may include any configuration (e.g., strips, bars, segments, etc.) that covers the entirety or any portion of the basin 110. In addition, the heater element 200 may be implemented by any conventional or other type of heater or heating element (e.g., heating coils, etc.) that may be disposed on the basin at any suitable locations.

The temperature control unit 220 includes a device for adjusting current passing through heater element 200 so as to permit selective adjustment of the heat applied to the basin 110 (and thus the liquid in the basin). The power switch 125 permits selective application and removal of current flow with respect to the heater element 200. The heater element 200 is controlled by the controller 220 in accordance with an entered desired temperature and temperatures measured by a temperature sensor 230. The temperature sensor 230 is preferably implemented by a conventional resistive temperature device (RTD) (e.g., a 1,000 Ohm RTD). The sensor 230, however, may be implemented by any conventional or other type of temperature sensor, and may be disposed at any suitable location on the basin or within the cabinet housing 105. By way of example only, the temperature sensor 230 may be disposed adjacent the basin 110 to sense the temperature of the basin, the liquid contained therein, and/or the heater element 200. The sensor 230 is connected in series with a voltage source 240 and an indicator 250. The voltage source 240 and the power source 210 may be the same source, or the voltage for one may be derived from the other. The indicator 250 measures the current through temperature sensor 230, with the current being proportional to the sensed temperature. Both the indicator 250 and temperature controller 220 may correspond, for example, to the temperature controller/indicator 130 described above. For further examples of these types of heating units, reference is made to U.S. Pat. No. 5,333,326 (Faries, Jr. et al.) and U.S. Pat. No. 6,087,636 (Faries, Jr. et al.), the disclosures of which are incorporated herein by reference in their entireties.

It is to be understood that the thermal treatment system 100 described above and illustrated in FIG. 1 may have various configurations. For example, the thermal treatment system 100 may be configured to cool and/or congeal the medium to produce cooled liquid or surgical slush. In this instance, the heater element 200 may be replaced by refrigeration devices that are controlled in substantially the same manner described above. Furthermore, the thermal treatment system 100 may include a plurality of basins warming and/or cooling a sterile medium as described above. In addition, the system may be configured to attach to a stand (as shown in the figures) or another system cabinet or may be configured as a stand-alone unit. Examples of different types of system configurations are disclosed in U.S. Pat. No. 5,333,326 (Faries, Jr. et al.); U.S. Pat. No. 5,429,801 (Faries, Jr. et al.); U.S. Pat. No. 5,522,095 (Faries, Jr. et al.); U.S. Pat. No. 5,524,643 (Faries, Jr. et al.); U.S. Pat. No. 5,615,423 (Faries, Jr. et al.); U.S. Pat. No. 5,653,938 (Faries, Jr. et al.); U.S. Pat. No. 5,816,252 (Faries, Jr. et al.); U.S. Pat. No. 5,862,672 (Faries, Jr. et al.); U.S. Pat. No. 5,857,467 (Faries, Jr. et al.); U.S. Pat. No. 5,879,621 (Faries, Jr. et al.); U.S. Pat. No. 6,091,058 (Faries, Jr. et al.); and/or U.S. Pat. No. 6,255,627 (Faries, Jr. et al). The disclosures of the above-mentioned patents are incorporated herein by reference in their entireties.

The above described thermal system 100 may be utilized to heat a medical instrument such as a surgical scope. Surgical scopes (e.g., laparoscopes, endoscopes, arthroscopes, etc.) are used in corrective medical procedures, as well as in medical procedures that image interior viscera such as surfaces of the stomach, small intestines, and colon. The use of surgical scopes permits a surgeon to view a patient body interior with a minimal amount of cutting of patient tissue.

Figure 3:
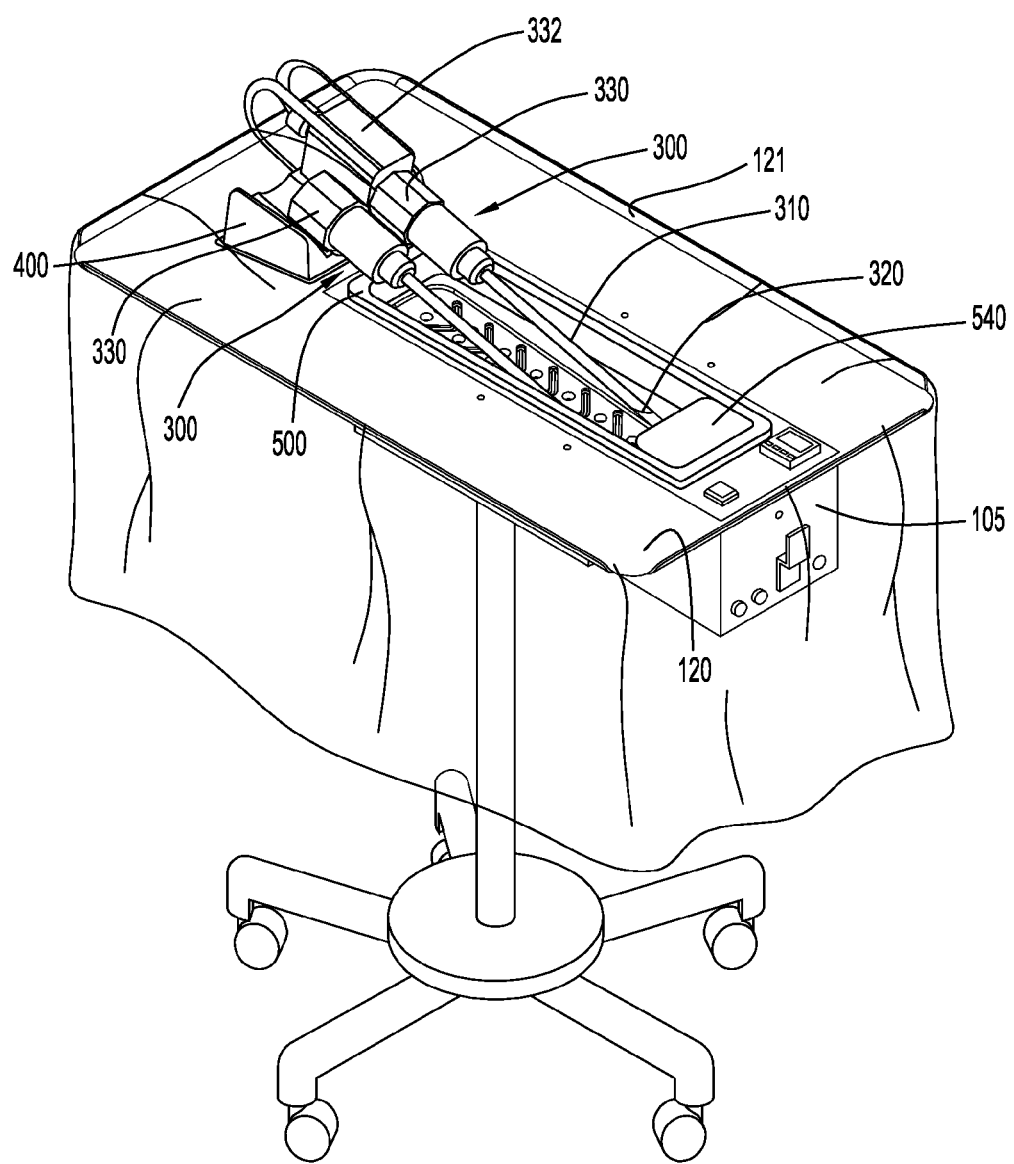
FIG. 3 illustrates a perspective view of a support assembly for a surgical instrument according to one embodiment of the invention, showing the support assembly coupled to the thermal treatment system of FIG. 1.

Referring to FIG. 3, a conventional or other surgical scope 300 typically includes a shaft member 310 with a distal portion 320 for insertion into a patient body. The distal portion 320 typically includes a lens operable to capture and transmit images. An optics unit 330 (e.g., a lens, attachment structure to facilitate connection with a camera, etc.) is disposed on the proximal end of the shaft member 310. Fiber optics (not shown) generally extend along the interior of the shaft member 310 to transmit image data from the distal end of the scope to the optics unit 330 for conveyance to the surgeon, for example, via an eyepiece, camera, or other device that may be coupled to the optics unit 330. As can be seen in FIG. 3, two surgical scopes 300 are shown in which each shaft member 310 is placed within the basin 110 so as to be substantially submerged in liquid within the basin. A support assembly comprising a ramp structure, as described in further detail below, supports the proximal end of each scope 300, where one scope includes both an optics unit 330 and camera 332 while the other scope includes only an optics unit 330.

When surgical scopes 300 are warmed prior to use, the scope optics (i.e., the optics unit 330 and camera 332) must remain dry to protect those optics and prevent distortion of the image. Scopes 300 are typically warmed in an insulated container (e.g., a THERMOS container) filled with warm liquid without temperature control. During treatment, the scopes come into contact with the sides and/or bottom of the container. The scopes 300 are warmed for several reasons, including enhancing image results, preventing infections, and maintaining normothermia. For example, a scope that is unwarmed prior to being inserted into a patient body may fog due to differences between the body temperature and scope temperature, thereby impeding or distorting the resulting image. Further, scopes may be warmed to minimize trauma caused to tissue in response to insertion of the scope into the patient body. The trauma basically results from the temperature difference between the scope and the tissue. Inserting a hot or cold scope may damage tissue, thereby leading to infections. Inserting a cold scope may lower the core body temperature of a patient, leading to hypothermia. A chemical wipe or spray may alternatively be used to reduce fogging; however, the chemical may be inadvertently introduced into the patient, thereby causing complications.

Accordingly, the present invention embodiments enable medical personnel (e.g., operating room staff, etc.) to warm scopes 300 in a controlled environment (e.g., liquid bath) while maintaining the scope optics 330 and/or camera 332 attached to the scope 300 in a dry state. In addition, the present invention embodiments provide a support system that stabilizes the scope, preventing its direct contact with the walls or floor of basin and/or with the drape.

Figure 5:
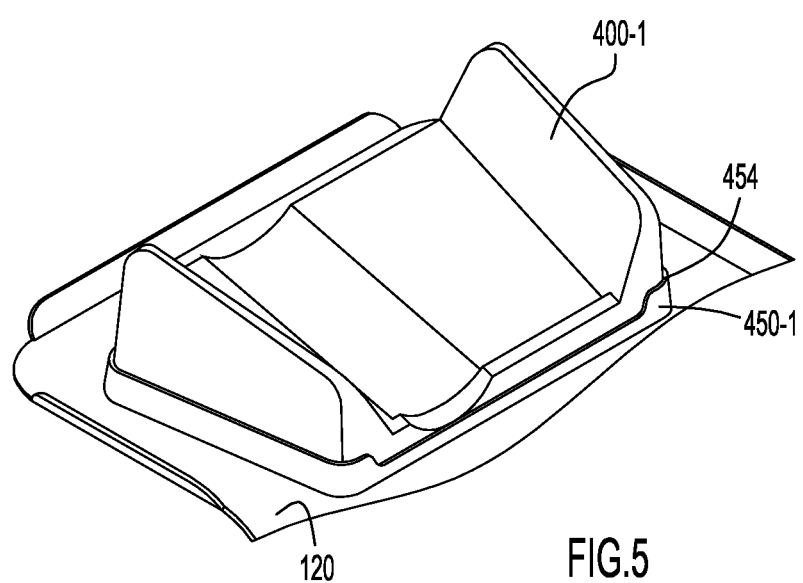
FIG. 5 illustrates a view in perspective of a support assembly for a surgical instrument coupled with the shelf (shown in part) of the thermal treatment system of FIG. 1 according to another embodiment of the invention.
Figure 6:
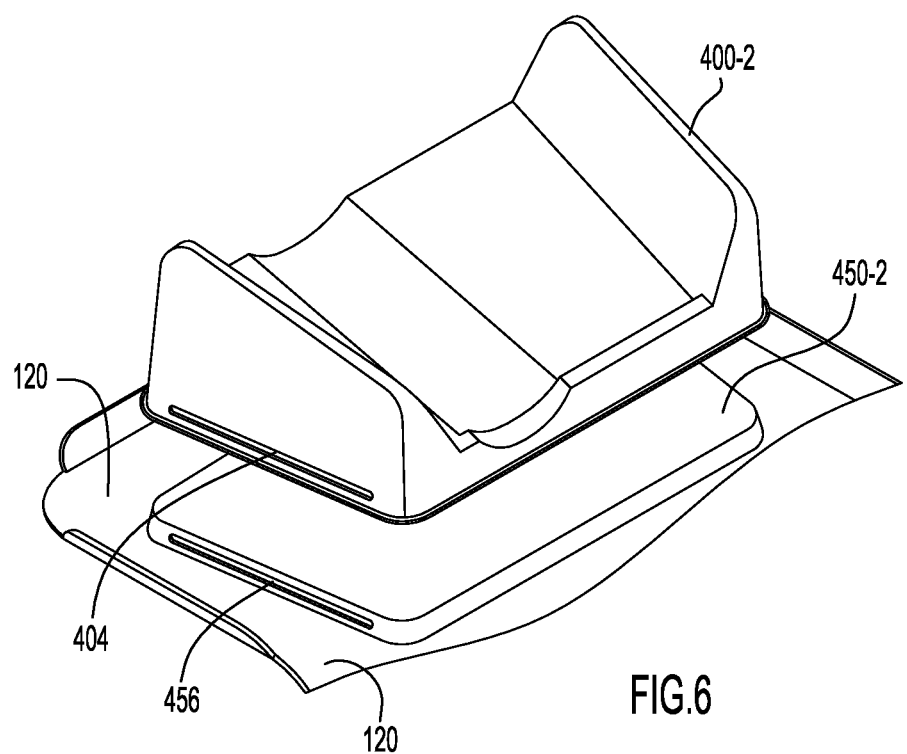
FIG. 6 illustrates an exploded view in perspective of a support assembly for a surgical instrument coupled with a shelf (shown in part) of the thermal treatment system of FIG. 1 according to a further embodiment of the invention.

In particular, the thermal treatment system 100 includes a support assembly comprising a ramp and a ramp mount. The ramp is operable to elevate optics unit 330 and/or camera 332 above the surface (fluid line) of the temperature-controlled, liquid bath contained in the basin 110. The ramp mount includes suitable structure to secure the ramp to a portion of the shelf 120 that is in close proximity to the basin 110. Any suitable structure can be provided to facilitate attachment or securing of the ramp structure to the shelf, and some non-limiting examples are depicted in FIGS. 4-6 and described below.

Figure 4:
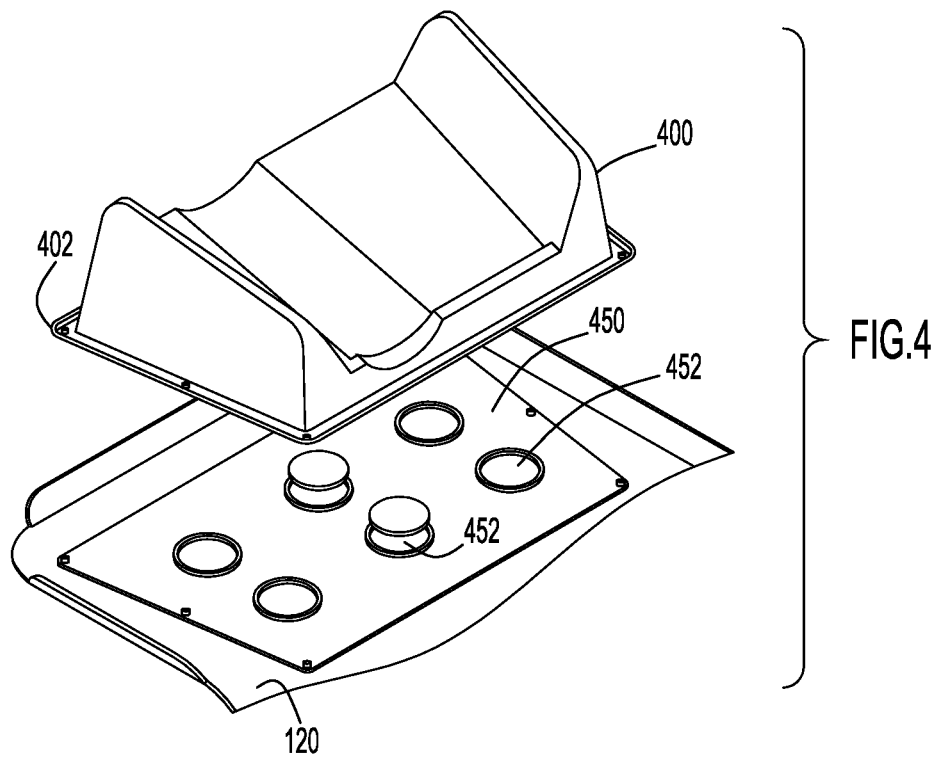
FIG. 4 illustrates an exploded view in perspective of a support assembly for a surgical instrument coupled with a shelf (shown in part) of the thermal treatment system of FIG. 1 according to an embodiment of the invention.

In a first example embodiment depicted in FIG. 4, a ramp 400 and ramp mount 450 are shown. The ramp mount 450 comprises a base plate that includes any suitable number (one or more) magnets 452 secured to one or both of the upper and lower surface of the ramp mount so as to facilitate a magnetic attraction and connection with a corresponding magnetic surface of the shelf 120 and/or with a corresponding magnetic surface disposed on an underside of the ramp 400. The ramp 400 includes a raised lip portion 402 that extends around the outer periphery of the lower surface of the ramp. The ramp 400 and ramp lip portion 402 are suitably dimensioned such that the lip portion 402 fits around outer peripheral edge portions of the ramp mount 450 when the ramp is connected with the ramp mount, where the lip portion 402 engages with the outer peripheral edge portions of the ramp mount 450 in a snap fitting engagement. The ramp 400 can further be bonded to the ramp mount 450 in any suitable manner to prevent removal of the ramp from the ramp mount (e.g., via heat welding to seal the ramp with the ramp mount). In an alternative embodiment in which magnets are not provided in the ramp mount, the ramp mount 450 can be affixed directly to a portion of the cabinet shelf 120 in any other suitable manner including, without limitation, using ultrasonic energy, heat welding, solvents, adhesives, RF welding techniques, mechanical affixing via screws or other fasteners, or any other appropriate or conventional attachment process.

The ramp and ramp mount can be constructed of any one or more suitable, medical grade materials including, without limitation, silicone or other suitable plastics and/or metal materials such as stainless steel. For embodiments in which magnets are used to secure the ramp mount to a surface portion of the shelf and/or to secure the ramp to the ramp mount, each of the ramp and shelf further include suitable magnetic materials to facilitate securing by magnetic attraction of the ramp and/or shelf to the magnets disposed on the ramp mount.

The design of the support assembly as depicted in FIG. 4 facilitates arrangement of the drape in a number of different configurations with respect to the ramp 400 and ramp mount 450. For example, in embodiments in which the ramp mount is removably secured to the cabinet shelf (e.g., via the use of magnets for the ramp mount and a corresponding magnetic surface for the shelf), the drape can be placed upon the shelf 120 prior to assembly of the ramp 400 and ramp mount 450 upon the shelf, such that the drape is disposed between the ramp mount and the cabinet shelf. In another embodiment, the ramp 400 and ramp mount 450 can first be connected to the cabinet shelf 120, followed by placement of the drape over the cabinet shelf. In this embodiment, the drape can be disposed over the shelf 120, ramp 400 and ramp mount 450 or, alternatively, over just the cabinet shelf while leaving the ramp and ramp mount exposed. In a further embodiment, the drape can be placed over the shelf 120 and ramp mount 450 secured to the shelf, followed by securing of the ramp 400 to the ramp mount 450 such that the drape is disposed between the ramp and the ramp mount. In embodiments in which the ramp and/or ramp mount are not covered by the drape, the ramp and/or ramp mount are preferably provided in a sterile condition for use with the system 100 (e.g., the ramp and/or ramp mount can be provided in a sterilized package prior to use). In addition, the drape can be designed with a cut-out section or other suitable geometry that provides for substantial or complete coverage of the cabinet shelf while leaving the ramp and/or ramp mount uncovered and exposed. The embodiments depicted in the figures show the ramp and ramp mount secured to the shelf and exposed with the drape not overlying or covering these components.

In a second example embodiment depicted in FIG. 5, a ramp mount 450-1 is configured in the form of a boot that is secured in any suitable manner to the cabinet shelf 120 (e.g., in any of the ways described above for the embodiment of FIG. 4). The ramp mount 450-1 includes outer lip portions 454 that extend upward and away from the shelf 120 along the peripheral edges of two opposing sides of the ramp mount. The ramp mount 450-1 and ramp 400-1 are suitably dimensioned such that the ramp 400-1 fits between the lip portions 454 so as to be firmly secured or fixed to the cabinet shelf 120 via the ramp mount 450-1. Like the previous embodiment, the ramp and ramp mount can be constructed of any suitable materials including, without limitation, silicone or other medical grade plastics or metal materials. When the ramp 400-1 is seated on the ramp mount 450-1 between the lip portions 454, the ramp is held in a frictional fit engagement within the ramp mount. This allows the ramp to be removed from the ramp mount after use for disposal or recycle (i.e., re-sterilization and re-use). Alternatively, the ramp 400-1 can be secured to the ramp mount 450-1 using any suitable technique (e.g., using ultrasonic energy, heat welding, solvents, adhesives, RF welding techniques or any other appropriate or conventional attachment process). As with the previous embodiment of FIG. 4, the drape can be placed between cabinet shelf and ramp mount, placed between ramp mount and ramp, placed over the cabinet shelf, ramp mount and ramp, or placed over the cabinet shelf while leaving ramp and ramp mount exposed during system operation.

Figure 6A:
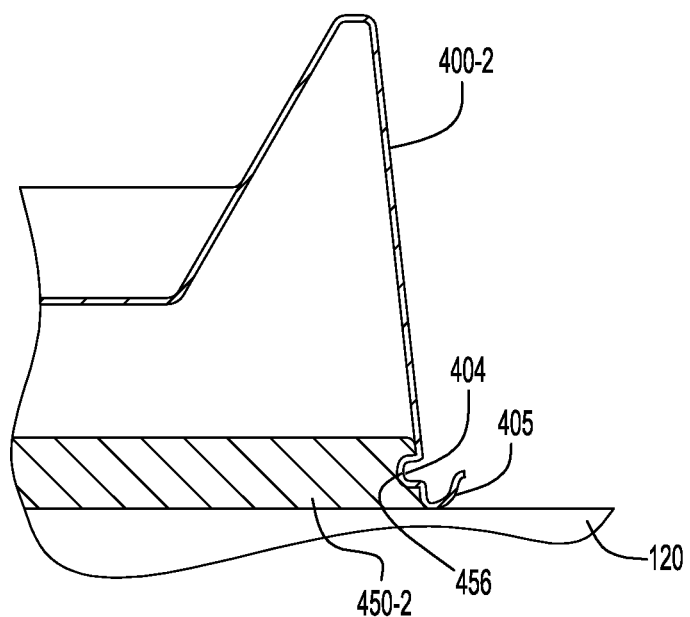
FIG. 6A illustrates a partial view in cross-section of the support assembly of FIG. 6.

In the embodiment of FIG. 6, a ramp mount 450-2 comprises a generally rectangular base plate including indentations or grooves 456 extending along opposing side wall surfaces of the base plate. The ramp mount 450-2 can be secured in any suitable manner to the cabinet shelf 120 (e.g., in any of the ways described above for the embodiment of FIG. 4). The ramp 400-2 includes lip portions extending along the lower edges of the opposing wall surfaces of the ramp that correspond with the opposing surfaces of the ramp mount 450-2 including grooves 456. As can be seen from the cross-sectional view of the ramp depicted in FIG. 6A, each of the lip portions of the ramp 400-2 include an inwardly extending tab 404 that extends along the side wall surface of the ramp and a rolled edge 405 that has a generally U-shaped cross-sectional configuration. As can also be seen from the cross-sectional view in FIG. 6A, the ramp 400-2 has a hollow interior and, upon placement of the ramp over the ramp mount, the lower sidewall surface portions of the ramp are frictionally fit around the ramp mount 450-2 with tabs 404 fitting and locking within grooves 456 in a snap fitting connection. This allows the ramp 400-2 to be snap fit and removably secured to the ramp mount 450-2, where the rolled edges 405 of the ramp can be pressed to dislodge tabs 404 from grooves 456 when it is desired to remove the ramp from the ramp mount. Thus, the ramp 400-2 can be disposed after a single use or recycled (re-sterilized) for additional uses. Like the other embodiments of FIGS. 4 and 5, the ramp and ramp mount can be constructed of any suitable materials including, without limitation, silicone or other medical grade plastics or metal materials, preferably using materials that facilitate suitable flexibility and resiliency of the rolled edge portions to facilitate removal of the ramp from the locked engagement with the ramp mount. In addition, as with the previous embodiments, the drape can be placed between cabinet shelf and ramp mount, placed between ramp mount and ramp, placed over the cabinet shelf, ramp mount and ramp, or placed over the cabinet shelf while leaving ramp and ramp mount exposed during system operation.

Figure 7:
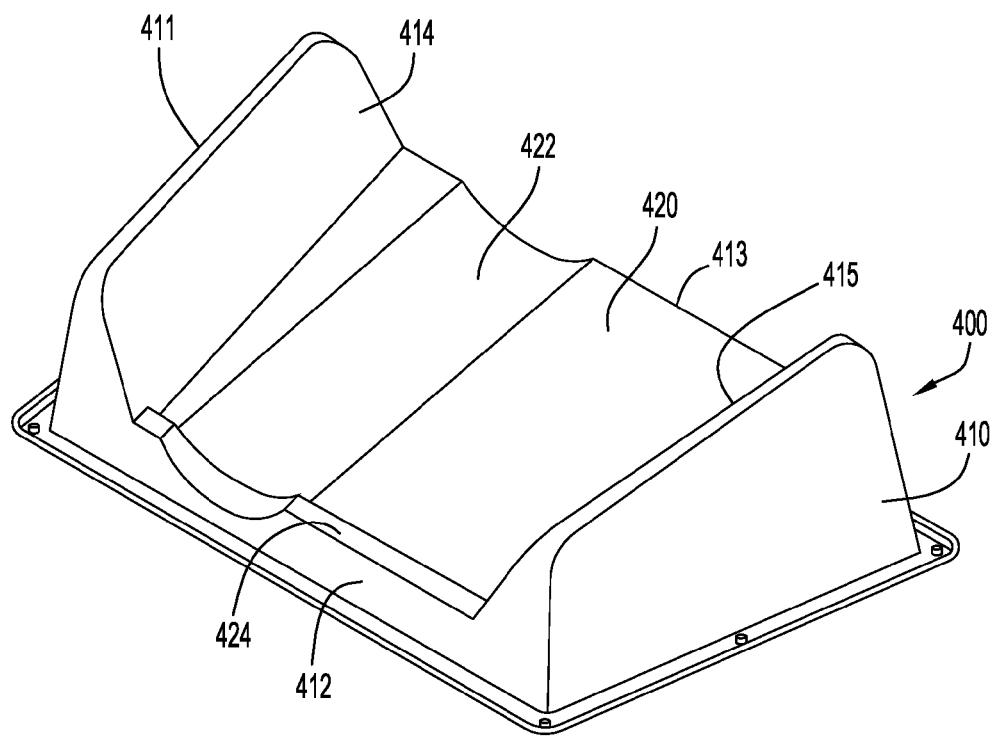
FIG. 7 illustrates a view in perspective of a portion of a support assembly in accordance with an embodiment of the invention, the support assembly including a ramp for supporting portions of surgical instruments that are thermally treated using the thermal treatment system of FIG. 1.

The ramp is designed to support one or more scopes at their proximal ends including optics components. Referring to FIGS. 3 and 7, ramp 400 includes exterior side walls 410, 411, front wall 412 and rear wall 413. For certain embodiments (such as the ramp 400-2 of FIG. 6), the ramp is at least partially hollow between its front, rear and side walls to facilitate insertion of at least a portion of the ramp mount 450 within the ramp during connection of the ramp and ramp mount. As further described for the embodiments of FIGS. 4 and 6, the ramp can also include a lip portion at its lower peripheral edges to provide a locking (e.g., snap fitting) engagement with the ramp mount.

Ramp 400 includes an angled and multi-faceted upper wall or scope receiving portion that includes a slot and various angled or inclined surfaces designed to support and retain optics components at the proximal end of a scope 300 (e.g., the optics unit 330 and camera 332) during thermal treatment of one or more scopes with system 100. In particular, the scope receiving portion of the ramp 400 includes opposing interior side walls 414, 415 that correspond with exterior side walls 410, 411. Each interior side wall 414, 415 is tapered or angled outward and toward its corresponding exterior side wall 410, 411 such that a distance between the interior side wall and its corresponding exterior side wall decreases in a direction from a lower end of the ramp 400 that connects with ramp mount 450 to an upper, free end of the ramp. In an example embodiment, each interior side wall 414, 415 can extend outward at an angle of about 30° or less, where the angle is measured at the intersection between the interior side wall and an imaginary plane that is oriented parallel with respect to the cabinet shelf 120 when the ramp is connected with the shelf. The angled interior side walls 414, 415 minimize side movement and provide increased or enhanced stability for one or more scopes supported by the ramp 400 during system operation.

The scope receiving portion further includes a generally planar camera receiving surface 420 and a generally rounded, concave slot 422 defined within the camera receiving surface 420. The camera receiving surface 420 and concave slot 422 are angled at a suitable ramped incline as these surfaces extend from the front wall 412 to the rear wall 413. As can be seen in FIG. 3, camera receiving surface 420 is suitably dimensioned to receive, hold and retain the camera 332 of a first scope 300, while at least a portion of the shaft 310 including distal end 320 of the scope is submerged in thermal treatment liquid within the basin 110. In addition, a second scope 300 can also be held by the ramp 400 simultaneously with the first scope, where the concave slot 422 receives, holds and retains the optics unit 330 of the second scope while at least a portion of the shaft 310 including the distal end 320 of the second scope is submerged in thermal treatment liquid within the basin 110. The front wall 412 includes a lip portion 424 that extends slightly above and beyond surface 420 and slot 422 so as to provide an abutting ledge or stop for portions of the camera 332 and optics unit 330. In particular, the lip portion 424 of the front end wall 412 provides a stop which prevents the camera and optics unit from sliding down the ramp 400 and into the basin 110 during thermal treatment of the first and second scopes.

The dimensions of the scope receiving portion as well as other portions of the ramp 400 are configured to hold portions of one or more scopes with suitable stability. For example, the dimension of each interior side wall 414, 415 between the camera receiving surface 420 and the upper, free end of the ramp 400 can be suitably dimensioned to engage with at least about ⅓ of a corresponding surface portion of the scope camera 332 when the camera is placed on surface 420. In addition, the width dimension of the ramped or inclined scope receiving portion that includes camera receiving surface 420 and concave slot 422 at the front end wall 412 of the ramp 400 can be the same or similar to the width dimension defined between the vertical side walls 175 of the basin 110. Further, the width dimension between exterior side walls 410, 411 at the front end wall 412 of the ramp 400 can be the same or similar to the width dimension between exterior side wall surfaces of the cabinet housing 105.

Figure 8:
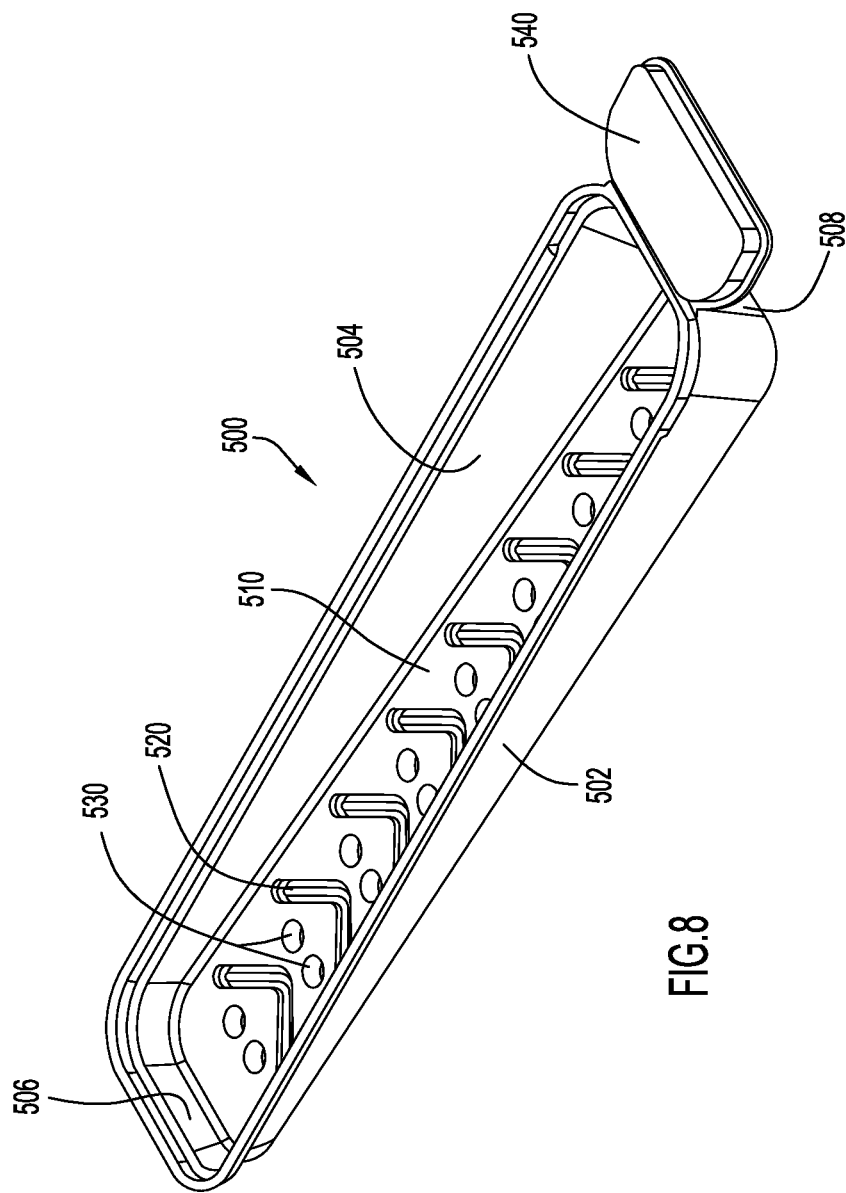
FIG. 8 illustrates a view in perspective of a tray for use with the thermal treatment system of FIG. 1.

Referring to FIGS. 3 and 8, a tray 500 is provided that is suitably dimensioned and configured to be inserted within the basin 110 of the system 100, where the tray has length and width dimensions that are slightly smaller than those of the basin. The tray 500 is constructed of suitable materials including, without limitation, medical grade plastics and/or metal materials, to prevent puncture of the tray by medical instruments that are placed and thermally treated within the tray. For example, as noted above, the tray can be made of a heavy gauge polyethylene/ionomer resin blend having a thickness of approximately 10 to 16 mils, where the percentage of ionomer resin in the blend can be in the approximate range of forty to seventy percent. The tray 500 can further be designed for placement above or below the drape 170 that is placed within the basin 110.

In a preferred embodiment, the tray 500 is designed to overlay the drape 170 (i.e., the drape is disposed between the basin and the tray) in order to protect the drape from puncture or rupture during thermal treatment of medical items and thus ensure a sterile barrier is maintained during system operation. In addition, in certain embodiments, the tray 500 provides a bather between the scope 300 and the drape 170 to protect the drape from potentially overheating and melting due to light irradiation from a light source disposed within the scope. As noted above, the tray 500 can be integrated with the drape 170 so as to be a single unit or, alternatively, the tray can be designed as a separate component that can be placed over the drape after the drape is inserted within the basin 110. For example, the tray can be integrated with the drape to form a single unit using any suitable technique such as ultrasonic energy, heat welding, solvents, adhesives, RF welding techniques or any other appropriate or conventional attachment process. In embodiments in which the tray is in direct contact with medical instruments, the tray is sterilized (either with the drape when both are integrated as a single unit, or separately from the drape) prior to being used.

The tray 500 includes side walls 502, 504, a front wall 506, a rear wall 508, a bottom wall 510 and a reservoir defined between the walls to receive thermal treatment fluid when the tray is placed within the basin 110. The bottom wall 510 of the tray 500 tapers to form a decline or ramped surface from the front wall 506 to the rear wall 508 of the tray. Thus, when the tray 500 is placed within the basin 110, a gap is formed between the generally horizontal floor 180 of the basin and the bottom wall 510 of the tray, where the gap increases in dimension as the bottom wall 510 extends from the rear wall 508 to the front wall 506 of the tray.

The bottom wall 510 of the tray 500 further includes a plurality of indentations or grooves 520 having a general V-shape, where the grooves 520 are aligned along the lengthwise dimension of the bottom wall. A plurality of generally circular openings or holes 530 are also provided extending through the bottom wall 510 of the tray 500 and arranged along the lengthwise dimension of the bottom wall and at spaced locations between and/or on either side of the V-shaped grooves 520. As depicted in FIG. 8, two holes 530 are provided on either side of each V-shaped groove 520. However, any other suitable number, arrangement and/or configuration of holes and grooves can be provided along the bottom wall of the tray. The grooves 520 provide a frictional, non-smooth contour for the interior surface of the bottom wall 510 so as to enhance stabilization of the scope shaft member 310 within the tray and to further prevent slipping of the scope camera 332 and/or scope optics unit 330 from the ramp 400 into the thermal treatment fluid within the tray reservoir. The holes 530 facilitate the flow and circulation of thermal treatment fluid between the tray reservoir and the gap formed between the basin floor 180 and the bottom wall 510 of the tray, which prevents stagnation of the thermal treatment fluid and promotes enhanced thermal treatment of medical items disposed within the tray reservoir.

Figure 9:
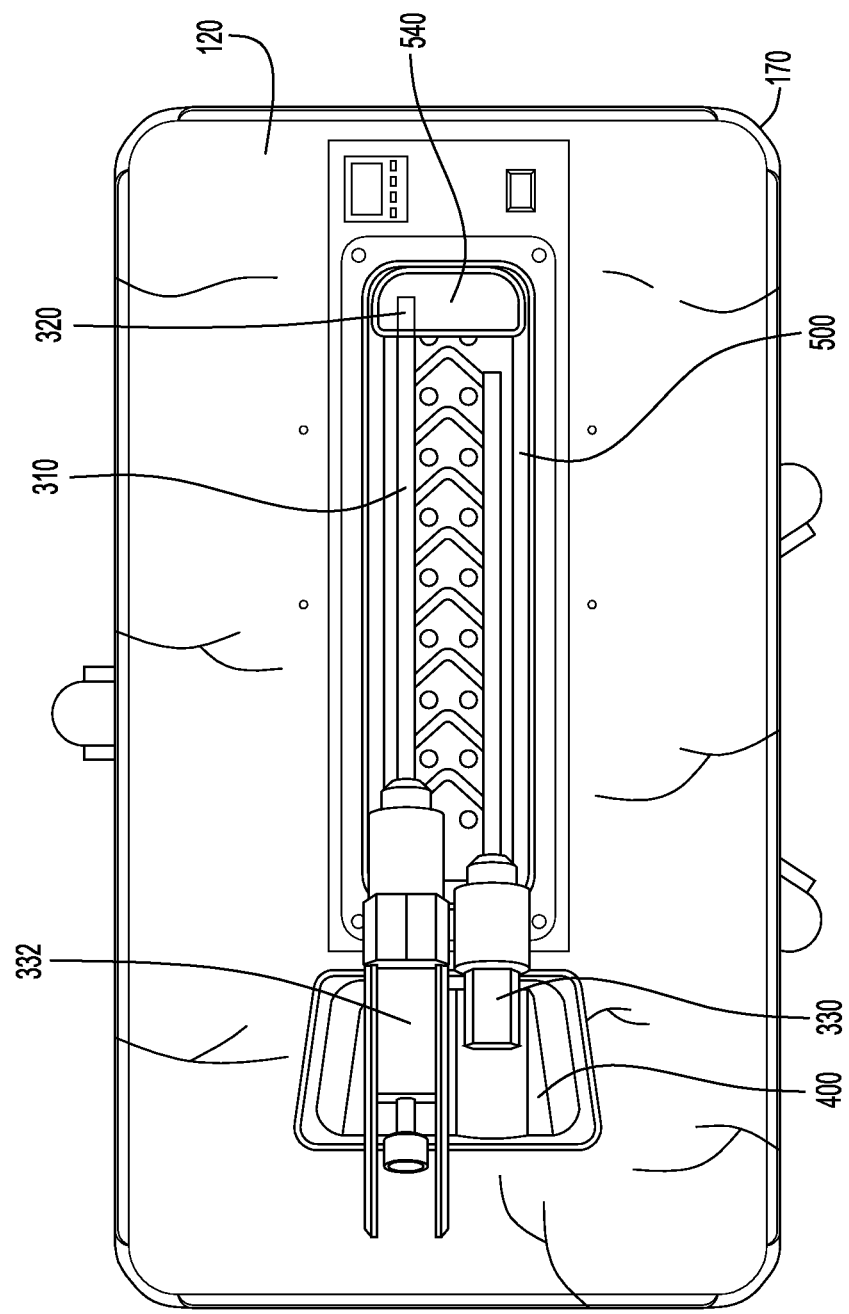
FIG. 9 illustrates a top view in plan of the support assembly for a surgical instrument and tray coupled to the thermal treatment system of FIG. 3.

A top wall 540 of the tray 500 is coupled via a hinge connection with rear wall 508 so as to facilitate a partial closing or forming a partial cover over the tray reservoir. For example, in embodiments in which the tray is constructed of a suitable medical grade plastics material, the hinge connection can comprise a plastic material of reduced thickness in relation to the top wall 540 and bottom wall 510 which forms a "living hinge" connection to allow bending and pivotal movement of the top wall with respect to the bottom wall. The top wall 540 is depicted in an open position in FIG. 8, whereas the top wall 540 is flipped (via the hinge connection) to a closed position overlying the reservoir as depicted in FIG. 9. The hinged top wall 540, when in its closed position overlaying the reservoir, is suitably dimensioned to cover a portion of the shaft member 310 of scope 300 including distal end 320 when the camera 332 of the scope rests upon the camera receiving surface 420 of the ramp 400 (as can be seen in FIG. 9). This further enhances the stability of the system in maintaining portions of the scope within the thermal treatment fluid while preventing portions such as the camera and optics unit of the scope from inadvertently falling within the tray reservoir.

A further feature of the tray 500 is that interior wall portions within the reservoir of the tray 500, including rear wall 508 and/or any other portions that face the distal end 320 of the scope shaft member 310 when the scope is thermally treated within the tray reservoir, are white in color. The one or more white colored interior wall portions within the tray allows for calibration of the camera (e.g., via white balancing) while it is being thermally treated by the system 100.

Operation of the system is described with reference to FIGS. 1-9. The system 100 is initially set up by installing the ramp 400 and/or ramp mount 450 with respect to the cabinet shelf 120 in the manner described above (e.g., utilizing any of the embodiments of FIGS. 4-6). The drape 170 and tray 500 are also installed in the basin in the manner described above, with the drape 170 and tray 500 extending within the basin 110 and the drape further extending over the cabinet shelf 120 and optionally over the ramp 400 and/or ramp mount 450. A sterile treatment fluid is provided within the reservoir of the tray 500 and basin 110.

The portion of the shaft member 310 including distal end 320 of a first scope 300 is placed in the reservoir of tray 500 while the camera 332 is placed on camera receiving surface 420 of the ramp 400. In addition, a second scope 300 can also be thermally treated (as shown in FIG. 3) at the same time as the first scope by placement of the shaft member 310 including distal end 320 of the second scope within the tray reservoir while placing scope optics unit 330 within the concave slot 422 of the ramp 400. The corresponding sloped or ramped camera receiving surface 420 and tray bottom wall 510 ensure that a sufficient portion of the scope shaft member 310 including distal end 320 for each of the first and second scopes is submerged in thermal treatment fluid within the tray reservoir. In addition, the lip portion 424 and design of the scope receiving portion of the ramp 400 as well as the grooves 520 in the tray bottom wall 510 prevent or substantially limit the potential for the scope camera 332 of the first scope and the scope optics units 330 of the first and second scopes from slipping off the ramp 400 and falling into the tray reservoir. Therefore, the scope optics unit for each scope and also the camera for the first scope is maintained in a dry state, while the scope shaft member 310 for each scope is primarily placed into the thermal treatment fluid bath within the tray reservoir.

The sterile thermal treatment bath disposed within the tray reservoir and within the basin 110 can be heated (or cooled) to the desired temperature via manipulation of the controller 130 as described above and depicted in FIG. 2. Alternatively, the bath may be heated (or cooled) before any scope 300 is positioned in the ramp 400 and tray 500. The scope 300 absorbs the proper amount of thermal energy from the thermal treatment bath maintained within basin 110, while the optics unit 330 and camera 332 of the first and second scopes 300 remain dry, thereby preventing image distortion caused by liquid contacting exposed optics.

The holes 530 within the tray bottom wall 510 facilitate the circulation of thermal treatment fluid between the basin 110 and the tray reservoir, which prevents stagnation of the thermal treatment fluid and promotes uniform thermal treatment of each scope. The ramp 400 and the top wall 540 and grooves 520 of the tray 500 effectively stabilize each scope as it is thermally treated by system 100. This allows for accurate temperature warming of selected portions of the scope, which, in turn, reduces tissue trauma, maintains normothermia, and enables the scope optics unit to remain dry for clear viewing of images. In addition, puncture or damage to any one or more of the scope 300, the basin 110, or the drape 170 is avoided since the tray 500 prevents the distal end 320 of the scope from directly contacting the basin or drape.

The system can be modified such that the cabinet shelf 120 has a different configuration from that which is depicted in FIGS. 1-9. Referring to FIGS. 10-12, a thermal treatment system is depicted in each figure that is substantially similar to the system of FIGS. 1-9, with the exception that the cabinet shelf 120 has a different geometric design.

In the embodiment of FIG. 10, the cabinet shelf 120-1 has a generally rectangular configuration with ledge portions that extend beyond the opposing side walls of the cabinet housing and raised edges 121 located along one or more sides of the shelf. The shelf 120-1 further includes a generally rectangular section 602 that extends from a longitudinal end of the shelf and has length and width dimensions that are smaller in relation to the rectangular portion of the shelf 120-1. The extended section 602 is suitably dimensioned such that the ramp 400 and ramp mount 450 are secured to this extended section. The ledge portions of the cabinet shelf 120-1 are suitably dimensioned to support tubing 600 connected with the scope 300. The tubing 600 typically contains wiring for the camera and scope (e.g., electrical wiring, fiber optic cables, etc.). The raised edges 121 of the shelf 120-1 provide a bather to prevent or inhibit the tubing 600 from falling off the shelf.

In the embodiment of FIG. 11, a generally rectangular shelf 120-2 (including raised edges 121 along one or more sides of the shelf) is provided that is offset from the cabinet housing 105 such that a ledge portion of the shelf extends beyond one side wall of the cabinet housing. This ledge portion is suitably dimensioned to receive and support tubing 600 connected with the scope 300.

In the embodiment of FIG. 12, the cabinet shelf 120-3 is aligned with respect to the cabinet housing 105 in a similar manner as that which is depicted in FIG. 11 (with a ledge portion of the shelf extending beyond one side wall of the cabinet housing and raised edges 121 along one or more sides of the shelf). In addition, shelf 120-3 further includes a generally rectangular section 604 that extends from a longitudinal end of the shelf and has length and width dimensions that are smaller in relation to the rectangular portion of the shelf 120-3. The extended section 604 is suitably dimensioned such that the ramp 400 and ramp mount 450 are secured to this extended section. Tubing 600 for the scope 300 is supported by the ledge portion of the shelf 120-3 and connects with the scope 300.

Other embodiments of the cabinet shelf are also possible that facilitate placement of the ramp and ramp mount on the shelf in proximity with the basin defined within the cabinet housing and further provides adequate surface area on the shelf to permit placement and support of tubing for fiber optics components and/or other instruments associated with the medical items being thermally treated by the system.

The shelf can be formed as part of the cabinet housing for system 100 or, alternatively, the shelf can be provided as a kit for retrofitting or after market installation with existing systems. In addition, the ramp and/or ramp mount can be included with the shelf in a kit or provided separately. Each of the shelf, ramp and ramp mount can be designed for disposal after a single use or, alternatively, recycled for additional uses (provided appropriate sterilization of the components has been applied between uses).

It will be appreciated that the embodiments described above and illustrated in the drawings represent only a few of the many ways of implementing a thermal treatment system instrument support assembly and method of selectively thermally treating medical instrument portions. For example, the present invention support assembly structure and/or thermal treatment systems are not limited to the applications described herein, but may be utilized for any types of medical or other items to selectively thermally treat any portions of those items.

In addition, the warming, cooling, ramp and ramp mount, support tray, basin systems and their corresponding cabinet housings and cabinet shelf sections, assemblies or housings may be of any shape or size and may be constructed of any suitable materials. The systems may include any quantity of heating and/or cooling basins in any combinations. The basin of the systems may be of any shape or size, may be constructed of any suitable thermal conducting materials (e.g., stainless steel, etc.), and may be disposed at any suitable locations on or within the housings. The systems may include any conventional or other heating and/or refrigeration units to thermally treat any type of sterile medium or other substance to any desired temperature. The heating unit may include any conventional or other heating device and components to control heating of a basin to any desired temperature (e.g., preferably to temperatures near (e.g., above, at or below) body temperature, such as temperatures in the approximate range of 60° F.-160° F.). The heater element may be of any quantity (e.g., at least one), shape or size, and may include any configuration (e.g., strips, bars, O-shaped segments, U-shaped segments or any other segments, etc.) that covers the entirety or any portion of a basin. The heater element may be attached to a basin via any conventional or other fastening techniques (e.g., any type of adhesives, brackets, etc.). In addition, the heater element may be implemented by any conventional or other type of heater or heating element (e.g., heating coils, etc.) that may be disposed on or proximate a basin at any suitable locations.

A cooling unit may include any conventional or other cooling or refrigeration device and components to control cooling of a basin to any desired temperature (e.g., preferably to temperatures near or below the freezing temperature of the sterile liquid or medium, such as temperatures in the approximate range of −32° F. to 32° F.). The various power switches and controllers of the systems may be implemented by any conventional or other power and control devices and may be disposed on the systems at any suitable locations.

The temperature sensor may be implemented by any conventional or other temperature sensing device (e.g., infrared, RTD, etc.) and may be disposed at any location on or proximate a basin or within the systems. The basins of the systems may be disposed in any arrangement or at any suitable locations on the systems. The systems may thermally treat (e.g., heat or cool) any type of medium or liquid, while a cooling basin may further include any type of conventional or other dislodgement mechanism, such as those described in the aforementioned patents.

The drapes employed with the heating, cooling and basin systems may be of any size or shape, and may be constructed of any suitable materials. The drapes are preferably transparent or translucent to facilitate manipulation of controls through the drape; however, these drapes may have any degree of transparency (e.g., including opaque). The drapes may be manipulated in any fashion with any portions of the drapes serving as a drape receptacle within a corresponding basin. The drapes may be of sufficient size to accommodate and form drape receptacles within any quantity of thermal treatment system basins. The drape may facilitate placement of any types of objects (e.g., instruments, containers, etc.)

within the basin. In addition, the drapes may be integrated in any suitable manner with any portion of the trays, ramps and/or ramp mounts.

The scope optics support assembly may be of any quantity, size or shape, may be disposed on any part of the drape and/or cabinet shelf and may be constructed of any suitable materials. The support assembly may be a separate unit or formed integral with and/or attached to the drape and/or preformed container portion via ultrasonic energy, heat welding, solvents, adhesives, RF welding techniques or any other attachment process. For example, the support assembly may include a ramp and ramp mount that are formed integral with each other, with the cabinet shelf and/or with the drape.

The shelf can be a separate unit that mounts to the cabinet housing or, alternatively, formed as an integral part of the cabinet housing. The shelf can have any suitable shape, design and configuration suitable to support the scope optics support assembly and provide surface areas for supporting components of the medical items being thermally treated by the system. The shelf can be constructed of any one or more suitable medical grade plastics, metals and/or other materials.

Any suitable ramp structure may be utilized that is capable of elevating objects above the basin floor and tray. The support members may include any quantity of support surfaces each to accommodate any quantity or portions of scopes or other objects. The support members may include any configuration to form support surfaces of any quantity, shape or size to receive any medical or other objects. The cabinet shelf may include any quantity of ramp structures and/or other support members disposed at any locations to elevate and/or submerge any portions of medical or other items. The ramp and ramp support can include any suitable configuration to facilitate mounting of the ramp structure to the cabinet shelf. The ramp can be formed integrally with the ramp mount or as a unit that is separable from the ramp mount. Similarly, the ramp mount can be formed integrally with the cabinet shelf or, alternatively, as a unit that is separable from the cabinet shelf. In addition, any one or more of the ramp, ramp mount, and cabinet shelf can be provided as a kit for installation and use with the thermal treatment system.

The trays can be configured to receive and submerge any number and types of medical items or portions of medical items. Any suitable number of openings and/or ridges or grooves may be provided in any internal wall portions of the trays to facilitate fluid circulation between the tray and basin and to further enhance stability of the medical items placed within the tray. Any suitable number of top wall portions can be provided for the tray to selectively close one or more portions of the tray reservoir. The tray can be designed as a disposable unit limited to a single use. Alternatively, the tray can be configured for re-sterilization and re-use. The tray can be integrated with or provided as a separate unit from the drape.

The control circuit, power port, fuse holders, and/or other components may be disposed within the systems at any suitable locations and may be implemented by any conventional or other circuitry components arranged in any desired fashion to perform the described functions. The temperature controller may be implemented by any conventional or other temperature controller and include any desired devices for entering a temperature (e.g., buttons, keypad, etc.). The basin power switch of the systems may be implemented by any conventional or other switching device, while the fuses may be implemented by any conventional fuse or other limiting device and may be configured for any current or voltage levels. The power cord may be implemented by any conventional or other cord or cable and be configured to accommodate any desired power signals. The system may utilize any type of power source (e.g., batteries, wall outlet jack, AC, DC, etc.).

It is to be understood that the terms "top", "bottom", "front", "rear", "side", "height", "length", "width", "upper", "lower", "vertical" and the like are used herein merely to describe points of reference and do not limit the present invention to any particular orientation or configuration.

From the foregoing description, it will be appreciated that the invention makes available a novel thermal treatment system instrument support assembly and method of selectively thermally treating medical instrument portions, wherein a system thermally treats surgical scopes and/or other medical instruments in a temperature controlled liquid bath while maintaining optics of the scope (or other portions of the instruments) in a dry state.

What is claimed is:

1. A thermal treatment system for thermally treating objects comprising:
   a housing including a top surface;
   a basin recessed into the top surface and configured to contain a liquid medium, wherein the liquid medium thermally treats objects placed within the liquid medium; and
   a ramp structure disposed on the top surface of the housing, the ramp structure being configured to support at least one object such that a first end portion of the object is disposed within the liquid medium while a second end portion of the object is supported by the ramp structure outside of the liquid medium.

2. The system of claim 1, wherein the ramp structure comprises a base that secures to the top surface and a ramp that secures to the base.

3. The system of claim 2, wherein the ramp is removably secured to the base with magnets.

4. The system of claim 2, wherein the ramp is removably secured to the base via a tab disposed on one of the ramp and the base that engages with a corresponding groove disposed on the other of the ramp and the base.

5. The system of claim 1, wherein the ramp structure includes an upper receiving surface that is angled and is configured to receive and retain a plurality of objects such that a first end portion of each object is disposed within the liquid medium while a second end portion of each object is supported by the upper receiving surface of the ramp structure outside of the liquid medium.

6. The system of claim 5, wherein the upper receiving surface includes at least one concave surface configured to hold and retain the second end portion of a first object and at least one planar surface configured to hold and retain the second end portion of a second object.

7. The system of claim 1, further comprising a drape disposed over at least a portion of the thermal treatment system and recessed within the basin to form a drape receptacle for the liquid medium.

8. The system of claim 7, wherein the drape covers at least a portion of the ramp structure.

9. The system of claim 7, wherein the ramp structure is affixed to the drape.

10. The system of claim 1, further comprising a tray suitably dimensioned to be removably disposed within the basin such that at least a portion of the liquid medium and the first end portion of each object are disposed within a reservoir of the tray.

11. The system of claim 10, wherein a bottom wall of the tray is ramped between two longitudinal end walls of the tray so as to form a gap between the tray and the bottom wall of the tray, the gap changing in dimension between the longitudinal end walls of the tray.

12. The system of claim 10, wherein the tray includes at least one of:
  (a) a plurality of grooves along an interior bottom wall surface of the tray, wherein the grooves provide a frictional, non-smooth contour for the interior bottom wall surface to enhance stabilization of the first end portion of each object disposed within the tray reservoir; and
  (b) at least one hole extending through the bottom wall surface of the tray to facilitate a flow and circulation of liquid medium between the tray reservoir and a gap formed between a bottom wall surface of the basin and the interior bottom wall surface of the tray.

13. The system of claim 10, wherein the tray includes a top wall that is secured with the tray and movable between first and second positions in relation to a top edge portion of the tray so as to partially cover an opening at the top edge portion of the tray when the top wall is in the first position and to not cover any portion of the opening when the top wall is in the second position.

14. The system of claim 10, wherein the at least one object comprises a scope including a camera disposed at the second end portion of the scope, and an interior wall portion of the tray is white in color to facilitate calibration of the camera when the first end of the scope is aligned with the white interior wall portion of the tray.

15. The system of claim 1, further comprising:
  a shelf defined at the top surface of the housing proximate the basin, wherein the shelf is suitably dimensioned to support components of one or more objects being thermally treated by the system.

16. A surgical drape kit for use in a thermal treatment system including a housing with a top surface and a basin recessed within the housing top surface to contain and thermally treat a liquid medium, the drape kit comprising:
  a drape suitably dimensioned to cover and hang down from the top surface of the housing, the drape being disposed within and conforming to the basin to form a drape receptacle; and
  a ramp structure configured to be secured on the top surface of the housing, the ramp structure being configured to support at least one object such that a first end portion of the object is disposed within the liquid medium while a second end portion of the object is supported by the ramp structure outside of the liquid medium.

17. The surgical drape kit of claim 16, wherein the ramp structure comprises a base that is removably securable to the housing top surface and a ramp that secures to the base.

18. The surgical drape kit of claim 16, wherein the ramp structure includes an upper receiving surface that is angled and is configured to receive and retain a plurality of objects such that a first end portion of each object is disposed within the liquid medium while a second end portion of each object is supported by the upper receiving surface of the ramp structure outside of the liquid medium.

19. The surgical drape kit of claim 18, wherein the upper receiving surface includes at least one concave surface configured to hold and retain the second end portion of a first object and at least one planar surface configured to hold and retain the second end portion of a second object.

20. The surgical drape kit of claim 16, wherein the ramp structure is integral with the drape such that, in use, the drape underlies the ramp structure.

21. The surgical drape kit of claim 16, wherein the ramp structure is separate from the drape such that, in use, the drape covers at least a portion of the ramp structure.

22. The surgical drape kit of claim 16, further comprising a tray suitably dimensioned to be removably disposed within the basin such that at least a portion of the liquid medium and the first end portion of each object are disposed within a reservoir of the tray.

23. The surgical drape kit of claim 22, wherein a bottom wall of the tray is ramped between two longitudinal end walls of the tray so as to form a gap between the tray and the bottom wall of the tray, the gap changing in dimension between the longitudinal end walls of the tray.

24. The surgical drape kit of claim 22, wherein the tray includes at least one of:
  (a) a plurality of grooves along an interior bottom wall surface of the tray, wherein the grooves provide a frictional, non-smooth contour for the interior bottom wall surface to enhance stabilization of the first end portion of each object disposed within the tray reservoir; and
  (b) at least one hole extending through the bottom wall surface of the tray to facilitate a flow and circulation of liquid medium between the tray reservoir and a gap formed between a bottom wall surface of the basin and the interior bottom wall surface of the tray.

25. The surgical drape kit of claim 22, further comprising:
  a shelf configured to attach with the top surface of the housing proximate the basin, wherein the shelf is suitably dimensioned to support components of one or more objects being thermally treated by the system.

26. In a thermal treatment system including a housing with a top surface, a basin recessed into the top surface and configured to contain a liquid medium, and a ramp structure disposed on the top surface of the housing, a method of selectively thermally treating objects comprising:
  receiving an object within the basin such that a first end portion of the object is disposed within the liquid medium while a second end portion of the object is supported by the ramp structure outside of the liquid medium; and
  thermally treating at least the first end portion of the object submerged within the liquid medium.

27. The method of claim 26, wherein the thermal treatment system further includes a drape disposed over at least a portion of the thermal treatment system and recessed within the basin to form a drape receptacle for the liquid medium, and the ramp structure is affixed to the drape.

28. The method of claim 26, wherein the object comprises a scope including a camera disposed at the second end portion of the scope, wherein the camera is supported by the ramp structure and maintained in a dry state during thermal treatment of at least the first end portion of the scope that is submerged within the liquid medium.

29. The method of claim 28, wherein the thermal treatment system further includes a tray removably disposed within the basin such that at least a portion of the liquid medium and the first end portion of the scope are disposed within a reservoir of the tray.

30. The method of claim 29, wherein an interior wall portion of the tray is white in color, and the method further comprises:
  calibrating the camera when the first end of the scope is disposed within and aligned with the white interior wall portion of the tray.

31. The method of claim 26, wherein the thermal treatment system further includes a shelf defined at the top surface of the housing proximate the basin, and the method further comprises:

supporting components of one or more objects being thermally treated by the system on the shelf.

* * * * *